United States Patent [19]

Cavazza

[11] 4,021,435
[45] May 3, 1977

[54] DERIVATIVE OF NICOTINIC ACID WITH AMINES

[75] Inventor: Claudio Cavazza, Rome, Italy

[73] Assignee: Sigma-Tau Industrie Farmaceutiche Riunite S.p.A., Italy

[22] Filed: Mar. 19, 1976

[21] Appl. No.: 668,497

Related U.S. Application Data

[63] Continuation-in-part of Ser. No. 451,696, March 15, 1974, abandoned.

[52] U.S. Cl. .................. 260/294.8 D; 260/295.5 A; 424/266
[51] Int. Cl.$^2$ ...................................... C07D 213/56
[58] Field of Search ............ 260/294.8 D, 247.7 V, 260/243 B; 424/266

[56] References Cited

UNITED STATES PATENTS

| | | | |
|---|---|---|---|
| 2,647,120 | 7/1955 | Williamson et al. | 260/294.8 D |
| 3,086,976 | 4/1963 | Borsy et al. | 260/247.7 V |
| 3,268,526 | 8/1966 | Newallis et al. | 260/243 B |

Primary Examiner—Alan L. Rotman
Attorney, Agent, or Firm—Robert E. Burns; Emmanuel J. Lobato; Bruce L. Adams

[57] ABSTRACT

A novel thiazolidide ester of nicotinic acid is disclosed having the formula:

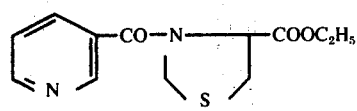

The compound has the useful pharmacological activity of lowering cholesterol, free fatty acid and triglyceride plasma levels in cases of malfunctioning lipid metabolism.

A synthesis of the compound from nicotinoyl chloride hydrochloride or nicotinic acid is described as well as modes for the administration of the compound.

1 Claim, 2 Drawing Figures

EFFECT OF $ST_{61}^*$, 245 MG/KG S.C., ON LIPID MOBILIZATION IN 17-HOUR FASTED RATS (A) AND IN NOR-ADRENALINE 1 MG/1 ML/KG S.C. TREATED RATS (B). RATE ±E.S.M. OF FAST INDUCED LIPOLYSIS WAS 907±72 μEq/L. RATE ±E.S.M. OF NOR-ADRENALINE INDUCED LIPOLYSIS WAS 804±32μEq/L (10 PER GROUP). STUDENT'S "t" TEST VS CONTROLS. Δ INDICATE A P=.001 SIGNIFICANT DIFFERENCE.

* THIAZOLIDIDE 4-CARBOXYLIC ETHYL ESTER OF NICOTINIC ACID

EFFECT OF $ST_{61}^*$ ON NOR-ADRENALINE □—·—·—□ (0.15 MCG/ML) AND 3'5' AMPc ○--------○ (174.6 MCG/ML) STIMULATED LIPOLYSIS IN ISOLATED RAT EPIDIDYMAL ADIPOSE TISSUE. RATE ± E.S.M. OF NOR-ADRENALINE INDUCED LIPOLYSIS: 5.38±0.28 μEq/HOUR OF TISSUE; RATE ±E.S.M. OF 3'5' AMPc INDUCED LIPOLYSIS WAS 35±3μEq/gr/3 HOURS.

* THIAZOLIDIDE 4-CARBOXYLIC ETHYL ESTER OF NICOTINIC ACID

EFFECT OF ST₆₁*, 245 MG/KG S.C., ON LIPID MOBILIZATION IN 17-HOUR FASTED RATS (A) AND IN NOR-ADRENALINE 1 MG/1 ML/KG S.C. TREATED RATS (B). RATE ±E.S.M. OF FAST INDUCED LIPOLYSIS WAS 907±72 μEq/L. RATE ±E.S.M. OF NOR-ADRENALINE INDUCED LIPOLYSIS WAS 804±32 μEq/L (10 PER GROUP). STUDENT'S "t" TEST VS CONTROLS. Δ INDICATE A P=.001 SIGNIFICANT DIFFERENCE.

\* THIAZOLIDIDE 4-CARBOXYLIC ETHYL ESTER OF NICOTINIC ACID

EFFECT OF ST$_{61}$* ON NOR-ADRENALINE □—·—·—□ (0.15 MCG/ML) AND 3'5' AMPc O———————O (174.6 MCG/ML) STIMULATED LIPOLYSIS IN ISOLATED RAT EPIDIDYMAL ADIPOSE TISSUE. RATE ± E.S.M. OF NOR-ADRENALINE INDUCED LIPOLYSIS: 5.38±0.28 μEq/HOUR OF TISSUE; RATE ±E.S.M. OF 3'5' AMPc INDUCED LIPOLYSIS WAS 35±3 μEq/gr/3 HOURS.

* THIAZOLIDIDE 4-CARBOXYLIC ETHYL ESTER OF NICOTINIC ACID

DERIVATIVE OF NICOTINIC ACID WITH AMINES

RELATED APPLICATIONS

This application is a Continuation-in-Part of patent application Ser. No. 451,696 filed Mar. 15, 1974 and herewith abandoned.

FIELD OF THE INVENTION

This invention relates to the novel nicotinic acid ester, the thiazolidide-4-carboxylic ethyl ester of nicotinic acid and more particularly to its synthesis, utility and modes for its useful administration.

THE INVENTION

The compound: Thiazolidide-4-carboxylic ethyl ester of nicontinic acid having the formula:

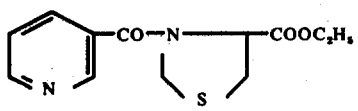

and its pharmaceutically acceptable salts have useful pharmacological activity related to lipid metabolism and indicated therapeutic activity in dislipidaemias.

DETAILED DESCRIPTION OF THE INVENTION

The invention above will be more fully described by the appended examples and by references to the drawing where:

Figure 1:
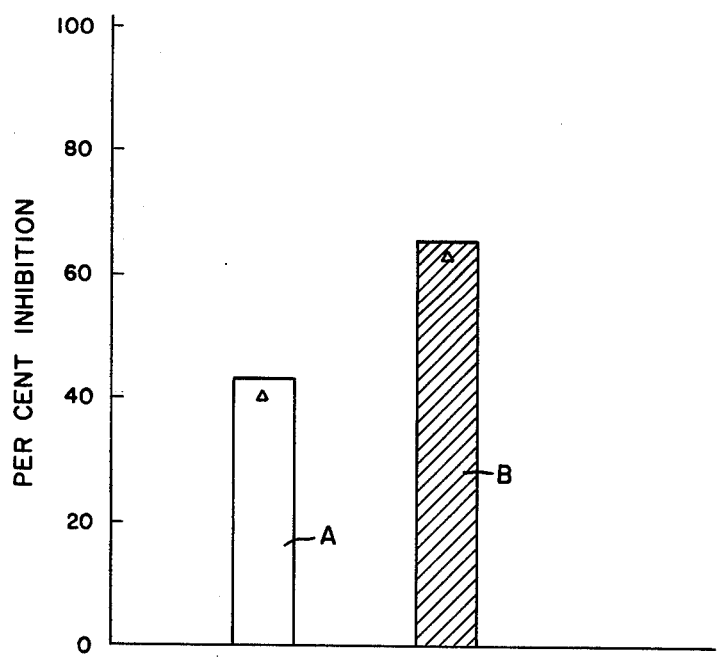
FIG. 1 shows the effect of the compound of the invention on lipid metabolism (FFA and triglycerides) in fasted rats.

The compound is prepared by reacting nicotinyl chloride hydrochloride or nicotinic acid esters with 4-thiazolidine carboxylic acid - ethyl ester in an anhydrous organic solvent inert to the reactants. Preferably the reaction is carried out in anhydrous chloroform, dioxane, tetrahydrofurane, (THF), N,N-dimethyl formamide (DMF). Chloroform is preferred. Part of the solvent medium may be an anhydrous proton or haloacid acceptor. Among such anhydrous acceptors are triethylamine, other trialkylamines, pyridine etc.

The reaction proceeds at temperatures between 15° and 90° C. Preferably the reaction provides a purer product in best yield at temperatures in the range 20°–30° C.

The product is purified by recrystallization from anhydrous acetone. The chromatographically pure product melts in the range 130°– 135° C.

The compound, the thiazolide-4-carboxylic ethyl ester of nicotinic acid, may be prepared into non-toxic pharmaceutically acceptable salts with organic acids such as acetic, citric, tartaric, salicylic, maleic etc. or with inorganic acids such as hydrochloric and hydrobromic acid, sulfuric acid, nitric acid, and phosphoric acid.

This compound (and its salts) has been found to be active pharmacologically by reducing cholesterol, free-fatty acid and triglyceride levels in plasma after administration.

The exact mode or situ of such activity in the organism is as yet unclear but the activity is unmistakable.

An additional factor of utility of the compounds for therapy is its low toxicity, and high therapeutic index.

The appended examples indicate a useful simple and preferred synthesis of the novel compound, its pharmacological activity and its therapeutic activity. The synthetic methods and the modes of administration are merely exemplary. All art-recognized equivalent methods and materials are intended.

EXAMPLE 1

Thiazolidide-4-carboxylic ethyl ester of nicotinic acid: (ST-61)

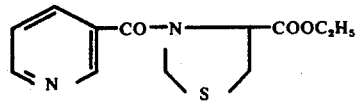

Suspend 1 mole of nicotinic acid chloride hydrochloride in anhydrous chloroform, slowly and under stirring add 1 mole of the 4-thiazolidinecarboxylic acid ethyl ester previously dissolved in anhydrous chloroform. The reaction vessel is equipped with a stirrer and a reflux condenser. The reaction mixture is maintained for 4 hours at 25° C with stirring. The reaction product is filtered. The chloroform solution is evaporated to dryness then the residue is recrystallized from acetone.

The melting-point of the chromatographically pure product obtained is = 130°– 135° C.

The elemental analysis confirms its composition as hydrochloride.

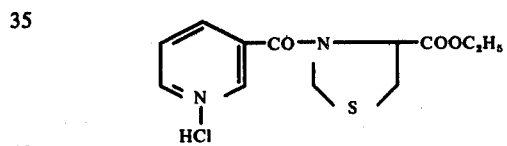

EXAMPLE 2

Toxicity

The compound of Example 1 (ST-61) has an $LD_{50}$ of 2500 mgm/kg per os in rats.

EXAMPLE 3

Pharmacological Activity

The pharmacological activity of the compound ST-61 was assessed by using the methods described in the following articles:

A — The antilipolytic activity in the fasting state was studied in accordance with 1. Carlson L. A. and E. R. Nye, Acute Effect of Nicotinic Acid In The Rat. Plasma and liver lipids and blood glucose.

Acta Med. Scand., 179, 453, 1966.

2. Dalton C., C. Van Trabert and J. X. Dwyer, Relationship of Nicotinamide and Nicotinic acid to Hypolipidemia, Biochemical Pharmacology, 19, 2609, 1970.

3. Bizzi A. and S. Garattini Drugs Lowering Plasma Free Fatty Acids: Similarities and Dissimilarities with the Nicotinic acid Effect, p. 207. K. F. Gey and L. A. Carlson Edrs. Hans Huber Publisher, Bern Stuttgard Vienna, 1971.

B — The antilipolytic activity in the case of Nor-Adrenaline stimulated lipolysis in rats was investigated in accordance with 1 — S. Garrattini and A. Bizzi Inhibiteurs de la mobilization des acides gras libres, Actualite Pharmacologiques XXII Serie, 169, 1969:

C — The antilipolytic activity in vitro was studied in accordance with

1. Monsigner B., M. Vanghan, Advances in Experimental Medicine and Biology Drugs affecting Lipid Metabolism, vol. 4, pag. 63 Edrs Holmes, Carlson, Paoletti Plenum Press New York 1969.

The new compound of Example 1 (ST-61) exhibited the following pharmacological activity in the above detailed tests: 1) hypolipidemic action: 245 mg/kg s.c. reduced the plasma levels of F.F.A. by 43 percent in the 17-h fasted rats and reduced the lipolytic activity of subcutaneously injected Nor-adrenaline by 65 percent in rats (FIG. 1).

Figure 2:
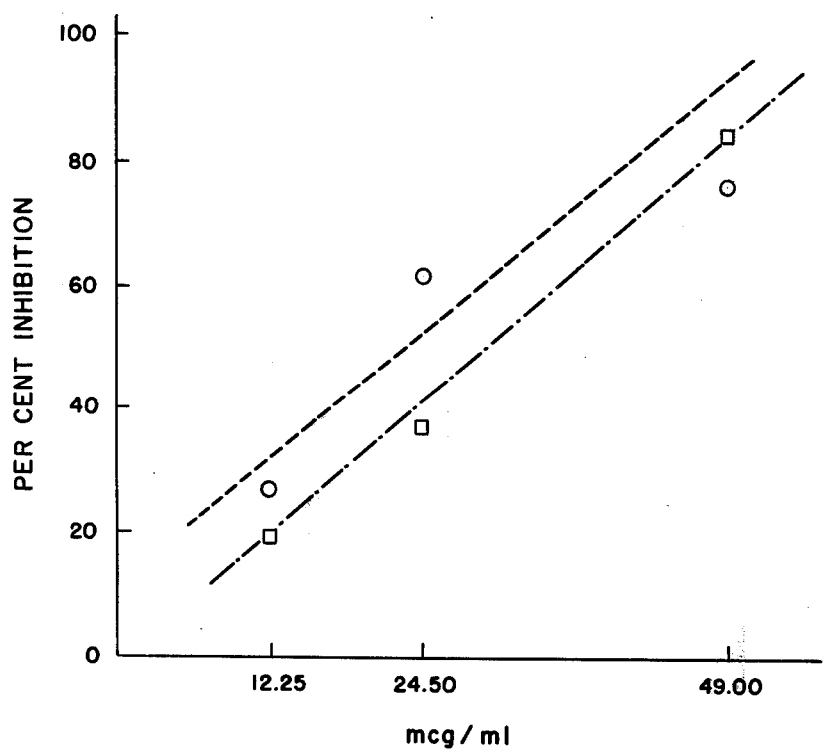
FIG. 2 shows the effect of the compound of the invention on nor-adrenaline and 3'5-AMPc-treated adipose tissue.

36.7 mcg/ml inhibited the "in vitro" lipolytic activity of 0.15 mcg/ml of Nor-adrenaline on rat epididymal adipose tissue by 85 percent, threshold dose 5 mcg/ml (FIG. 2) and 122 mcg/ml inhibited by 97 percent the "in vitro" F.F.A. release due to 176 mcg/ml of cyclic adenilate (FIG. 2).

The high therapeutic index of the compound was noted. $ST_{61}$, the thiazolidide 4-carboxylic ethyl ester of nicotinic acid clearly reduces hyperlipidaemic levels resulting from stimulated lipid mobilization and is useful in therapy where such activity is indicated as in dislipidaemias.

EXAMPLE 4

The various experimental animals used in the above tests were carefully observed and no untoward or unusual toxic syndromes were noted in other than the $LD_{50}$ test.

The invention includes within its scope pharmaceutical preparations containing, as an active ingredient, the therapeutically active compound, thiazolidide-4-carboxylic acid ester of nicotinic acid or the non-toxic acid addition salts thereof, in association with a pharmacologically acceptable carrier. Other therapeutic and compatible materials may be included in the preparation. The preparations may take any of the forms customarily employed for administration of therapeutically active substances, but the preferred types are those suitable for oral administration and especially tablets, pills and capsules including the substance. The tablets and pills may be formulated in the usual manner with one or more pharmacologically acceptable diluents or excipients, for example lactose or starch, and include materials of a lubricating nature, for example calcium stearate. Capsules made of absorbable material, such as gelatin, may contain the active substance alone or in admixture with a solid or liquid diluent. Liquid preparations may be in the form of suspensions, emulsions, syrups or elixirs of the active substance in water or other liquid media commonly used for making orally acceptable pharmaceutical formulations, such as liquid paraffin, or a syrup or elixir base. The active substance may also be provided when indicated, in a form suitable for parenteral administration, i.e. as a suspension or emulsion in sterile water or an organic liquid usually employed for injectable preparations, for example a vegetable oil such as olive oil, or a sterile solution in an organic solvent.

The following Examples illustrates the preparation of a pharmaceutical composition according to the invention.

EXAMPLE 5

25 g of thiazolidide-4-carboxylic ethyl ester of nicotinic acid 25 g of Avicel PH 101 (microcrystalline cellulose) and 25 g of Aerosil (highly purified silicon dioxide) are mixed together and gelatin capsules are filled each with the mixture so that each capsule contains 10 mg of active substance.

EXAMPLE 6

800 g of lactose and 200 g of maize starch are mixed with 200 ml of 5% maize starch in water. The mixture is granulated, dried at 550° C and sieved through a No. IV sieve (Sieve opening 0.7 mm). 1000 g of the granulate are mixed with 100 g of thiazolidide-4-carboxylic ethyl ester of nicotinic acid and gelatin capsules are filled each with the mixture so that each capsule contains 10 mg of the active substance.

What is claimed:

1. The compound: Thiazolidide-4-carboxylic ethyl ester of nicotinic acid having the formula:

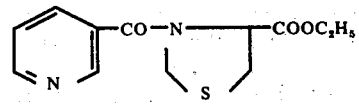

and the non-toxic, pharmacologically acceptable salts thereof.

* * * * *